(12) United States Patent
Isola et al.

(10) Patent No.: US 7,223,267 B2
(45) Date of Patent: May 29, 2007

(54) ULTRASONIC PROBE WITH DETACHABLE SLIDABLE CAUTERIZATION FORCEPS

(75) Inventors: Scott Isola, Deer Park, NY (US); Theodore A. D. Novak, King Park, NY (US); Alexander L. Darian, Huntington Station, NJ (US); Ronald R. Manna, Valley Stream, NY (US)

(73) Assignee: Misonix, Incorporated, Farmingdale, NY (US)

( * ) Notice: Subject to any disclaimer, the term of this patent is extended or adjusted under 35 U.S.C. 154(b) by 306 days.

(21) Appl. No.: 10/773,007

(22) Filed: Feb. 6, 2004

(65) Prior Publication Data

US 2005/0187512 A1 Aug. 25, 2005

(51) Int. Cl.
  *A61B 18/18* (2006.01)
  *A61B 17/32* (2006.01)
(52) U.S. Cl. .......................... 606/52; 606/169
(58) Field of Classification Search ............ 606/51, 606/52, 169, 205–207; 604/22
  See application file for complete search history.

(56) References Cited

U.S. PATENT DOCUMENTS

| | | | |
|---|---|---|---|
| 4,750,902 A | 6/1988 | Wuchinich et al. | |
| 4,931,047 A | 6/1990 | Broadwin et al. | |
| 5,013,312 A | 5/1991 | Parins et al. | |
| 5,383,883 A * | 1/1995 | Wilk et al. ................. | 606/169 |
| 5,630,837 A | 5/1997 | Crowley | |
| 5,776,092 A | 7/1998 | Farin et al. | |
| 6,024,741 A * | 2/2000 | Williamson et al. .......... | 606/40 |
| 6,056,735 A * | 5/2000 | Okada et al. ................. | 606/1 |
| 6,193,709 B1 * | 2/2001 | Miyawaki et al. ............ | 606/1 |
| 6,235,024 B1 | 5/2001 | Tu | |
| 6,293,946 B1 | 9/2001 | Thorne | |
| 6,394,973 B1 | 5/2002 | Cucin | |
| 6,508,765 B2 | 1/2003 | Suorsa et al. | |
| 6,723,092 B2 * | 4/2004 | Brown et al. ................. | 606/41 |
| 6,736,814 B2 * | 5/2004 | Manna et al. ................. | 606/50 |
| 6,773,409 B2 * | 8/2004 | Truckai et al. ................ | 601/2 |
| 6,860,880 B2 * | 3/2005 | Treat et al. ................... | 606/29 |
| 7,108,695 B2 * | 9/2006 | Witt et al. .................... | 606/41 |
| 2004/0064151 A1 * | 4/2004 | Mollenauer ................. | 606/205 |
| 2006/0259054 A1 * | 11/2006 | Masuda et al. ............ | 606/169 |

FOREIGN PATENT DOCUMENTS

WO    WO 87/06116    10/1987

* cited by examiner

*Primary Examiner*—Michael Peffley
(74) *Attorney, Agent, or Firm*—R. Neil Sudol; Henry D. Coleman; William J. Sapone

(57) ABSTRACT

A surgical device for ultrasonic ablation and RF cauterization includes a forceps member having at least one prong, the prong being formed as an electrode. At least one electrical connector is provided on the forceps member for operatively connecting the prong to an electrical power source. The surgical device further includes a mechanical connector attached to the forceps member for removably fastening the forceps member to a housing of an ultrasonic probe. The forceps member can thus function to carry out a cauterization procedure during a surgical operation utilizing the probe for ultrasonic ablation.

37 Claims, 5 Drawing Sheets

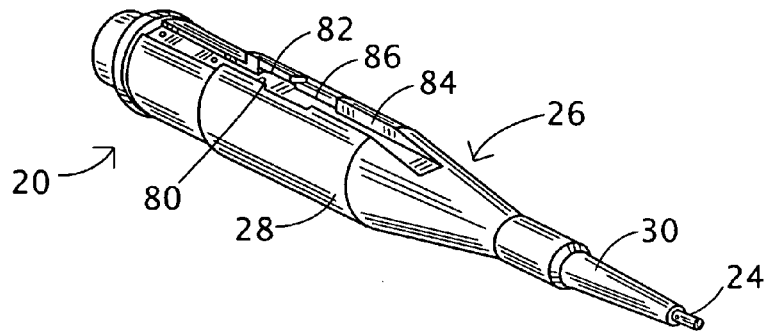
FIG. 7
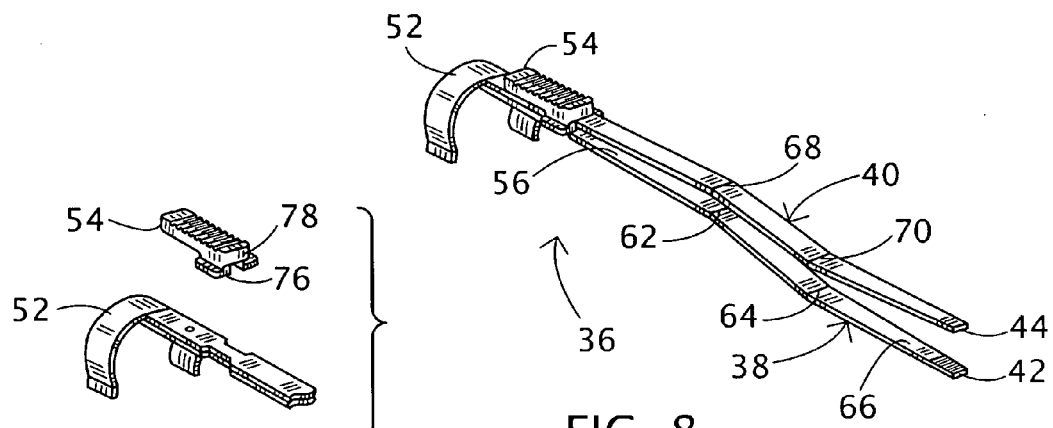
FIG. 8A
FIG. 8
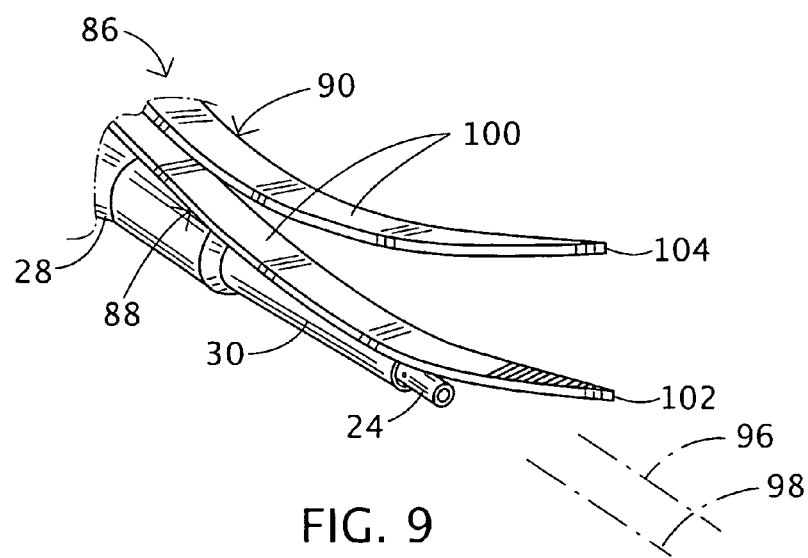
FIG. 9

ULTRASONIC PROBE WITH DETACHABLE SLIDABLE CAUTERIZATION FORCEPS

FIELD OF THE INVENTION

This invention relates to a medical device and more specifically to an ultrasonic tissue ablation instrument. Even more specifically, this invention relates to an ultrasonic medical treatment device with electrocautery. This invention also relates to an associated medical treatment method.

BACKGROUND OF THE INVENTION

Many diseases of the brain and spine require surgery to provide the patient with relief. These could include cancer, non-malignant lesions and trauma induced by accidents or physical attack. As a procedure, neurosurgery has been practiced for several millennia. Archaeologists have discovered evidence of sophisticated cranial surgery in relics and skulls dating back to Roman times. The tools found have been shown to be remarkably similar to today's designs. Of course, modern science has substantially improved upon the techniques and results obtained in those days.

One of the biggest steps forward occurred approximately 30 years ago with the invention and marketing of the ultrasonic surgical aspirator. This device utilizes a hollow probe or tool that vibrates at frequencies at or above 20 kc with tip amplitudes of up to 300 microns. When the vibrating tip is placed against viable or diseased tissue, the moving tip ablates the cells and causes them to fragment or otherwise emulsify in the irrigation fluid that is being added simultaneously. The emulsified fluid is then aspirated through the hollow probe and deposited in a canister for histological examination or disposal.

The advantage of excising tissue with this device is that the surgeon can remove the lesion in layers almost 5 cells thick. By slowly removing the tumor from the top down, he can clearly see when he is reaching healthy tissue allowing him to stop before substantial collateral damage occurs. This is extremely desirable in brain and spine surgery, where tissue does not regenerate. Gastrointestinal surgeons have used the device as well for lesions of the liver and spleen, for the same reasons.

The required specifications, designs and engineering elements of such ultrasonic aspirators have become well known to the art in the intervening time. Although the technology is mature, several improvements can be made to enhance the ease of use and applicability to a wider range of procedures.

One side effect of any surgery is bleeding when the veins, arteries or capillaries are severed. Ultrasonic surgery is more sparing of blood vessels than knives because the collagen content of the vessels is more resistant to ultrasonic emulsion. However, the capillaries and small vessels will be compromised upon exposure to high amplitude ultrasonic tools. When these vessels are severed or punctured bleeding will of course occur. The surgeon will then be forced to pause the procedure, remove the ultrasonic tool from the site and generally reach for a cauterizing device of some type to close off the bleeder. Once coagulation has been achieved, then the surgeon can grab the ultrasonic tool, reposition it in the wound site and continue the removal of tissue. This situation repeats itself often in the course of the operation, lengthening the time of the procedure and coincidently the risk to the patient. It is therefore desired to find a way to cauterize tissue with the ultrasonic tool in place so the surgeon can stop bleeding with minimal downtime caused by switching tools and positions.

Several improvements to the basic design of the ultrasonic aspirator have been disclosed over the years, which allow some degree of cauterization subsequent to or simultaneously with ultrasonic ablation. Most center on the application of RF cautery currents to the tool or probe itself. This has the effect of turning the ultrasonic tool into a monopolar RF cauterizer.

In a non-ultrasonic RF cauterizer, the tip of the tool is energized with a voltage sometimes exceeding 3000 volts RMS. The frequency of the voltage is very high, in order to prevent cardiac arrest in the patient. These frequencies are generally greater than 500,000 hertz. In monopolar RF, the tool is one pole of the electrical circuit. The second pole is generally a large piece of metal foil which the patient lays on during the procedure. The bare skin touching the foil makes an effective electrical contact. As the tool touches the tissue and the RF voltage is energized, a complete circuit path is created. The currents are very high, reaching 5 amps in some cases. At these currents, significant joule heating occurs in the tissue, raising the temperature higher than the burning temperature of 42° C. Continued operation dries the tissue by evaporating the water content. Cauterization then occurs. Since the back plate is very large in relation to the tool tip, the current "fans out" as it leaves the tool tip and thereby lowers the current density in the tissue to a point where the temperature rise in the tissue is reduced to that below burning. This minimizes collateral burning and tissue damage.

However, as large as the plate is, some collateral damage occurs away from the bleeder site. This collateral damage cannot be controlled reliably by the physician and is of great concern when operating on the brain. If the damage is too widespread, mental capacity or nerve structures may be affected negatively. In addition, electrical current is forced to flow through viable tissue to the ground plate. Again, neurological damage may occur in some organs that are susceptible to damage due to this current, such as the brain, heart and nerve bundles. Other organs, such as the liver or spleen, are less susceptible to current effects.

Researchers have found a way to minimize or eliminate this current path by designing a tool that includes two electrical poles or contacts. This is called bipolar RF cauterization. Here the current flows between the two poles through the intervening tissue. No current path to the back is allowed. Therefore, the tissue that is damaged is only that caught between the two contacts, which can be very small.

Designers have found a way to add monopolar cautery to ultrasonic devices by connecting one electrical contact to the vibrating tip of the ultrasonic device. Several patents have disclosed concepts and techniques for this, such as U.S. Pat. No. 4,931,047 to Broadwin, et al. Here, the tip of the ultrasonic tool is the single pole that touches the tissue. The surgeon will generally stop ultrasonic vibration and turn on the cautery voltage. Current leaves the tip of the probe and goes through the body to the back plate. This has been shown to be effective in eliminating the need for switching tools to stop bleeding, saving time and effort on the doctor's part. However, all of the detriments of monopolar cautery still exist. Neurosurgeons are especially reticent to allow significant current to flow through brain or spinal cord tissue for fear of inducing neurological damage. In addition, the piezoelectric crystals of the ultrasonic transducer stack must be isolated from the cautery voltage or damage to the transducer or electronics will occur.

OBJECTS OF THE INVENTION

It is an object of the present invention to provide an improved ultrasonic ablation probe with electrocautery.

It is a more specific object of the present invention to provide such an ultrasonic ablation and cauterization probe assembly with improved cauterization function.

Another relatively specific object of the present invention is to provide such an ultrasonic ablation and cauterization probe assembly where the cauterization function is optionally utilizable.

A further object of the present invention is to provide such an ultrasonic ablation and cauterization probe assembly with enhanced visualization.

These and other objects of the present invention will be apparent from the drawings and descriptions herein. Although every object of the invention is believed to be attained by at least one embodiment of the invention, there is not necessarily any single embodiment that achieves all of the objects of the invention.

SUMMARY OF THE INVENTION

A surgical device in accordance with the present invention comprises a forceps member having at least one prong, the prong being formed as an electrode. At least one electrical connector is provided on the forceps member for operatively connecting the prong to an electrical power source. The surgical device further comprises a mechanical connector attached to the forceps member for removably fastening the forceps member to a housing of an ultrasonic probe. The forceps member can thus function to carry out a cauterization procedure during a surgical operation utilizing the probe for ultrasonic ablation.

The mechanical connector may take the form of a spring clip with a slotted circular configuration for facilitating not only an attachment and subsequent detachment of the forceps member from the housing of the ultrasonic probe (for disposability, to ensure insulation integrity for each surgical procedure) but also a slidable fastening the forceps member to the housing of the probe so that the forceps member is alternatively movable in a distal direction and a proximal direction parallel to an axis of the probe.

The ultrasonic probe has the housing at a proximal end and a sheath at a distal end, the sheath being connected to the housing and surrounding the probe at a distal end thereof. Pursuant to another feature of the present invention, the forceps member is bent so that the prong conforms at a proximal end to the housing and at a distal end to the sheath. The word "conforming" is used herein to denote a structural configuration wherein the prong extends substantially adjacent and parallel to the respective portion of the probe casing, whether the housing or the sheath. Typically, the probe casing has a tapered configuration with a housing having a larger diameter than the sheath. In this case, the forceps member and particularly the prong is bent toward the sheath. In other words, where the forceps member includes a proximal end portion having an axis, the prong has a distal end portion bent away from the axis to lie along one side thereof (and close to the sheath). More specifically, where the probe has an axis and where the axis of the probe and the axis of the proximal end portion of the forceps member define a plane, the prong includes a first bend in the plane so that the distal end portion of the prong extends away from the axis of the proximal end portion of the forceps member and towards the axis of the probe. Pursuant to a further feature of the present invention, the prong includes a second bend so that the prong extends in part out of the plane of the forceps axis and the probe axis.

In one embodiment of the present invention, the prong includes a third bend generally towards a distal tip of the probe. In this case, the prong is provided with a V-shape portion disposed outside of the plane of the forceps axis and the probe axis, to provide better visibility of the tip. The third bend is located distally of the second bend, while the second bend is located distally of the first bend. In this embodiment and others, the prong has a distal tip distally advanced with respect to an operating tip of the probe in a distal position of the forceps member relative to the housing.

In at least one other embodiment of the present invention, the prong has a distal tip located substantially laterally of an operating tip of the probe.

The prong may be coated with an electrically insulating material, with a distal tip being free of the insulating material. Alternatively, the prong may be a polymeric member with an internal conductor.

In several embodiments of the present invention, the prong is one of two prongs of the forceps member. The prongs are preferably spring biased into an open configuration. In addition, it is preferably to provide the casing and the forceps member with cooperating locking elements for holding the prongs in a closed non-use configuration. Where the forceps member is slidably mounted to the casing for shifting alternately in a distal direction and a proximal direction, the cooperating locking elements may include a tab on at least one of the casing and the forceps member and a shoulder on the other of the casing and the forceps member for holding the prongs in the closed non-use configuration when the forceps member is slid in a proximal direction relative to the casing.

A medical method in accordance with the present invention comprises providing an ultrasonic probe having a casing or housing, providing a forceps member having at least one prong formed as an electrode, attaching the forceps member to the casing, inserting distal ends of the probe and the forceps member substantially simultaneously into a patient, thereafter energizing the probe with a standing ultrasonic compression wave to ablate tissues of a patient, manipulating the forceps member to clamp tissues of the patient after the inserting of the distal ends of the probe and the forceps member into the patient, thereafter delivering a radio-frequency electrical waveform to the forceps member to cauterize the clamped tissues, removing the probe and the forceps member from the patient, and thereafter detaching the forceps member from the casing. The manipulating of the forceps member includes pressing the prong against the probe, the probe functioning in part as a forceps prong.

According to another aspect of the present invention, the method further comprising moving the forceps member relative to the probe after the inserting of the probe and the forceps member into the patient and prior to the delivering of the radio-frequency electrical waveform to the forceps member. The moving of the forceps member preferably includes sliding the forceps member in a distal direction along the casing.

BRIEF DESCRIPTION OF THE DRAWINGS

FIG. 7 is a schematic perspective view of the ultrasonic instrument of FIGS. 1-6, with the cauterization forceps removed.

FIG. 8 is a schematic perspective view of the cauterization forceps of FIGS. 1-6, removed from the ultrasonic instrument.

FIG. 8A is an exploded partial view of the cauterization forceps and a manual actuator in the form of a tab or nub.

FIG. 9 is a schematic perspective view of a more distal end portion of the ultrasonic instrument of FIGS. 1-7 with a modified detachable cauterization forceps, in accordance with the present invention, showing the forceps in an extended position.

DETAILED DESCRIPTION OF THE PREFERRED EMBODIMENTS

Figure 1:
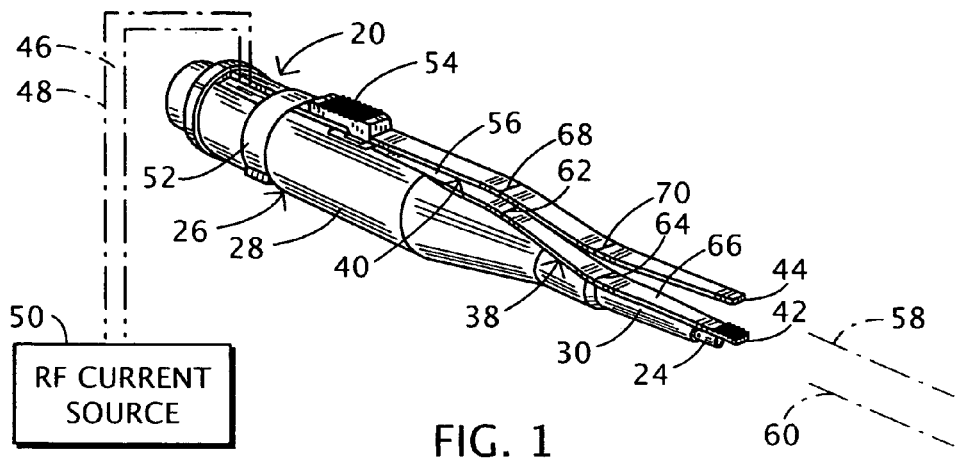
FIG. 1 is a schematic perspective view of a distal end portion of an ultrasonic instrument with a detachable cauterization forceps, in accordance with the present invention, showing the forceps in an extended or distally positioned, open configuration.
Figure 2:
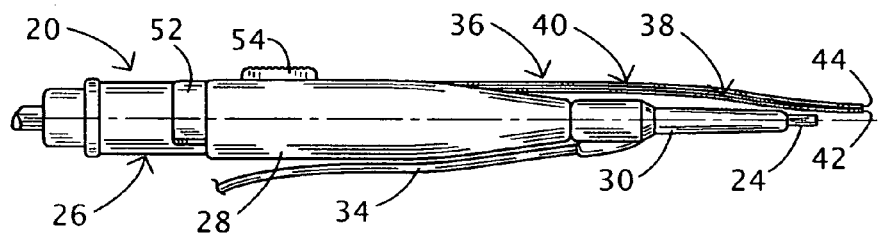
FIG. 2 is a side elevational view of the ultrasonic instrument and cauterization forceps of FIG. 1, showing the forceps in an extended closed configuration.

As illustrated in FIGS. 1-6, a surgical instrument assembly for ultrasonic ablation and RF cauterization includes an ultrasonic instrument 20 having an ultrasonic probe or horn 22 (FIG. 6) enclosed, except for an operative tip 24, in a casing 26. Casing 26 includes a housing portion 28 towards a proximal end of the instrument assembly and a sheath 30 at a distal end of the assembly. Casing further includes a handle (not shown) than is connected to a proximal end of housing portion 28 via an elbow joint (not shown). Sheath 30 surrounds a distal end portion of horn or probe 22. The ultrasonic instrument 20 further includes a piezoelectric transducer array (not shown) connected to a front driver 32 (FIG. 6) for generating ultrasonic standing waves in probe 22. A tube 34 is connected to casing 26 for irrigation. Suction is provided via an internal passage through the probe 22.

As illustrated in FIGS. 1-6, the surgical instrument assembly further includes a forceps member 36 having at least one prong (see FIGS. 14 and 15) formed as an electrode. In the embodiment specifically depicted in FIGS. 1-6, forceps 36 has two prongs 38 and 40 that act as RF frequency cauterization electrodes. Prongs 38 and 40 are provided, except at their distal tips 42 and 44, with an electrically insulating coating material. Prongs 38 and 40 may be plastic or polymeric material with internal conductors that project from the distal tips. Forceps 36 is provided with at least one electrical connector 46, in the case of monopolar operation, or two electrical connectors 46 and 48, for bipolar operation. Connectors 46 and 48 operatively connect prongs 38 and 40 to an electrical power source, particularly an RF current source, 50. Forceps 36 is further provided with a mechanical connector 52 in the form of a slotted circular spring clip for removably fastening the forceps member to housing 28 of instrument 20. The forceps member can thus function to carry out a cauterization procedure during a surgical operation utilizing instrument 20 for ultrasonic ablation.

Mechanical connector or spring clip 52 facilitates attachment and detachment of forceps 36 from probe housing 28 and also enables a slidable fastening of the forceps to the probe housing so that the forceps is alternately movable in a distal direction and a proximal direction parallel to an axis of instrument 20. This slidability facilitates use of forceps 36 for cauterization in alternation with use of probe 22 for ablation. If, for example, during the course of an ultrasonic ablation procedure, a blood vessel is nicked and starts to bleed, forceps 36 may be shifted in a distal direction from a non-use position (FIGS. 3-5) to an extended position (FIG. 1) for clamping and cauterizing the bleeding vessel. Forceps 36 is provided with a tab or nub 54 that facilitates a sliding of forceps 36 parallel to an axis of instrument 20, and particularly a distal end of probe 22.

Forceps 36 is bent so that inner prong 38 conforms at a proximal end to housing 28 and at a distal end to sheath 30, i.e., inner prong 38 extends substantially adjacent and parallel to housing 28 at the proximal end and to sheath 30 at the distal end. Probe casing 20 has a tapered configuration with housing 28 having a larger diameter than sheath 30. Forceps 36 and particularly inner prong 38 is bent toward sheath 30.

Forceps 36 and particularly inner prong 38 includes a proximal end portion 56 having an axis 58 extending generally parallel to an axis 60 of probe 22. Inner prong 38 has a distal end portion bent away from axis 58 to lie along an inner side thereof (closer to sheath 30). More specifically stated, axes 58 and 60 define a plane P1 and inner prong 38 includes a first bend 62 changing the orientation of the prong in the plane so that the prong 38 extends away from forceps axis 58 and towards probe axis 60. Inner prong 38 includes a second bend 64 also in the plane of axes 58 and 60 so that a most distal portion 66 of inner prong 38 so that inner prong 38 extends parallel to sheath 30.

Figure 3:
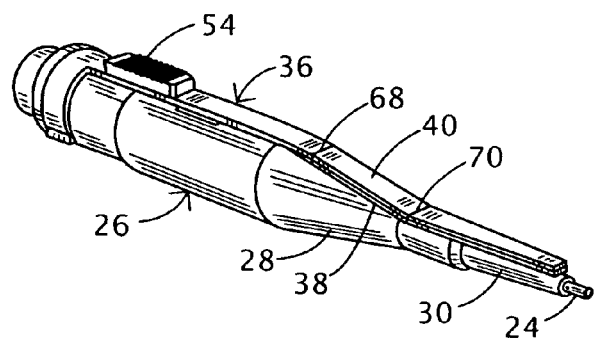
FIG. 3 is a schematic perspective view similar to FIG. 1, showing the forceps in a retracted or proximally positioned, closed configuration.
Figure 4:
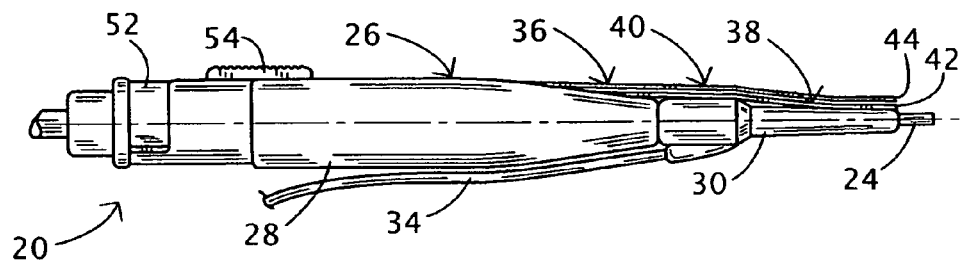
FIG. 4 is a side elevational view similar to FIG. 2, showing the forceps in the retracted closed configuration.
Figure 5:
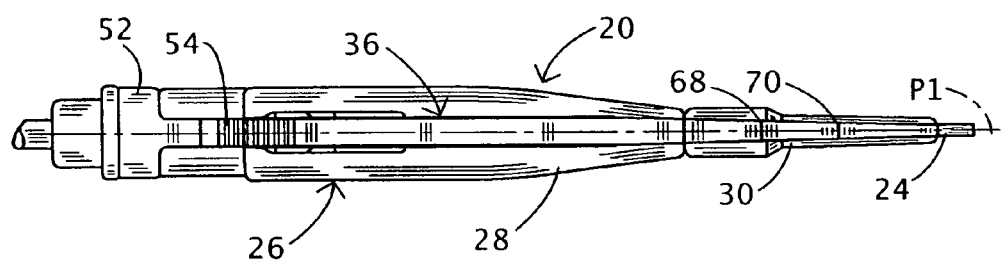
FIG. 5 is a top plan view of the ultrasonic instrument and cauterization forceps of FIGS. 1-4, also showing the forceps in the retracted closed configuration.
Figure 6:
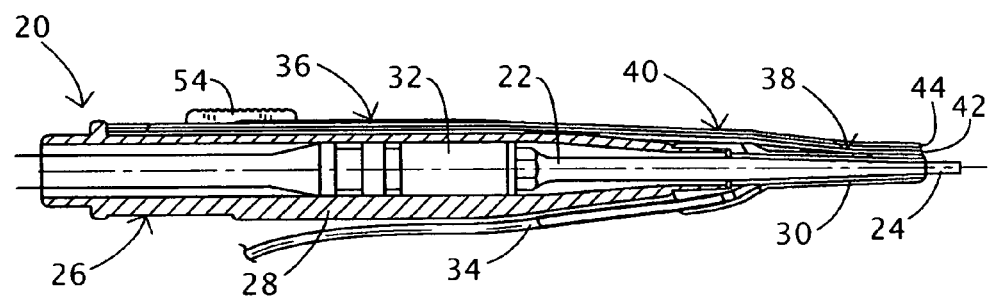
FIG. 6 is a longitudinal cross-sectional view of the ultrasonic instrument and cauterization forceps of FIGS. 1-5, also showing the forceps in the retracted closed configuration.

Inner prong 38 and outer prong 40 of forceps 36 are preferably spring biased to assume an open configuration (FIG. 1) upon a sliding of forceps 36 in a distal direction from the nonuse position (FIGS. 3-5). Outer prong 40 has a shape that is close to that of inner prong 38. (The tips may have a slight convergence angle to facilitate the application of pressure on a tissue structure at forceps closure: a gap may exist between the two prongs when the tips make contact.) Thus, outer prong 40 is formed with a proximal bend or angle 68 and a distal bend or angle 70 so that the prong conforms to housing 28 and sheath 30 of casing 26 particularly in the retracted non-use configuration (FIGS. 3-5) of forceps 36.

The user presses tab or nub 54 with the thumb to move forceps 36 from the retracted and closed non-use configuration (FIGS. 3-5) to the extended use position (FIG. 1). Under the action of the inherent spring bias of prongs 38 and 40, outer prong 40 separates from inner prong 38 (FIG. 1) during an extension stroke of forceps 36. In order to clamp a bleeding blood vessel or other tissue structure between tips of prongs 38 and 40, the user presses inwardly on tab or nub 54, i.e., towards housing 28, thereby closing the forceps towards a configuration depicted in FIG. 2. It is to be noted, with reference to FIG. 2, that in the extended position of forceps 36 distal tips of prongs 38 and 40 are located in a distally advanced position, i.e., more forward, than operative tip 24 of ultrasonic probe 22.

As shown in FIGS. 8, and 8A, tab or nub 54 is mounted to outer prong 40 and provided with a pair of wings 76 and 78 for effectuating an automatic forceps closure during a retraction stroke of forceps 36. During such a proximally directed motion of forceps 36, wings 76 and 78 engage, in a camming action, radially facing surfaces (not separately designated) of respective shoulders 80 and 82 (FIG. 7) on housing 28. That engagement forces outer prong 40 in a radially inward direction, towards inner prong 38 and probe casing 26. Shoulders 80 and 82 are disposed along an elongate slot 84 in casing 26 that also includes an expanded central segment 86 for receiving wings 76 and 78 during a mounting of forceps 36 to the casing.

Figure 10:
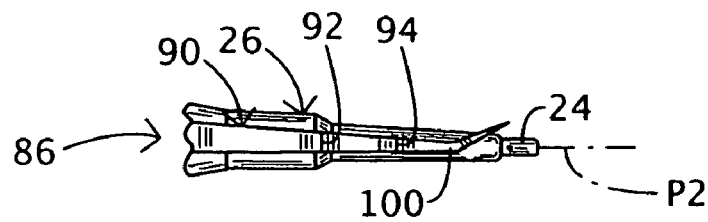
FIG. 10 is a partial top plan view of the ultrasonic instrument and cauterization forceps of FIG. 9, showing the forceps in a retracted position.

FIGS. 9 and 10 illustrate an embodiment of an ultrasonic probe assembly including the instrument 20 of FIGS. 1-6 and a modified RF cauterization forceps 86. Forceps 86 includes a pair of spring loaded prongs 88 and 90 each having not only a relatively proximal bend 92 and a relatively distal bend 94 in the plane P2 of a forceps axis 96 and a probe axis 98 but also a bend or curve 100 displacing the operative tips 102 and 104 of the prongs out of the plane P2 of axes 96 and 98. Bend or curve 100 is located distally of distal bend 94. In an extended position of forceps 86 (FIG. 9), operative tips 102 and 104 are located not only more distally than operative tip 24 of probe probe 22 but also substantially laterally thereto. Thus, whereas visualization of an operative site during ultrasonic ablation is facilitated by retraction of forceps 86, visualization of an operative site during cauterization is facilitated by the lateral displacement of forceps tips 102 and 104. In this regard, the lateral position of operative tips 102 and 104 with respect to instrument 20 means a lateral position with respect to the plane P2 of axes 96 and 98.

Figure 11:
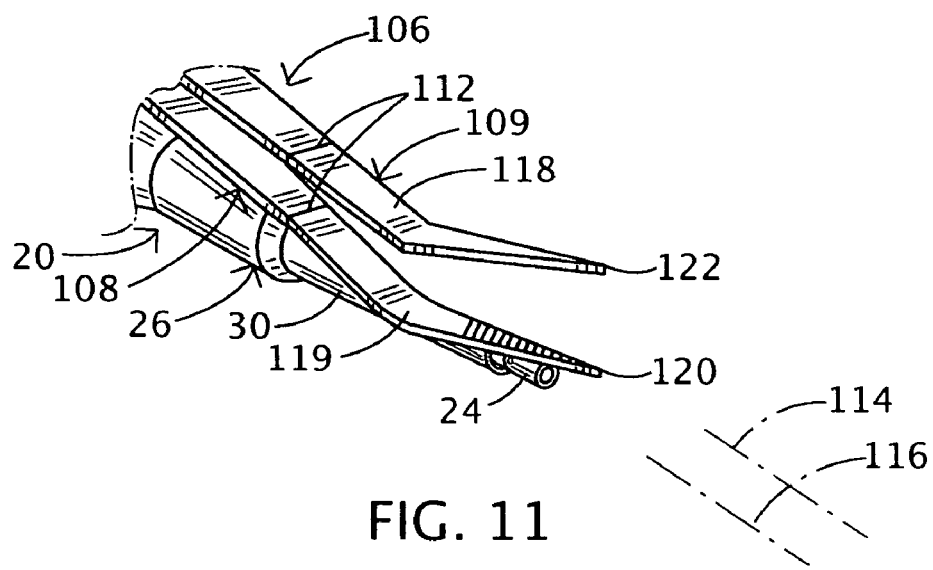
FIG. 11 is a schematic perspective view of a distal end portion of the ultrasonic instrument of FIGS. 1-7 with another modified detachable cauterization forceps, in accordance with the present invention, showing the forceps in an extended position.
Figure 12:
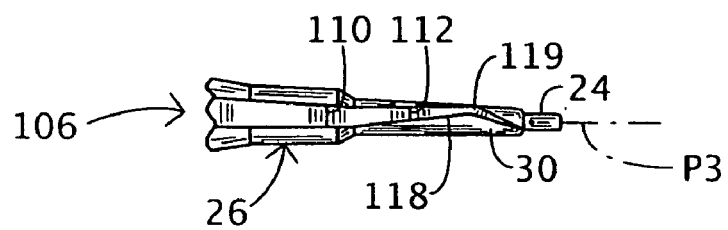
FIG. 12 is a partial top plan view of the ultrasonic instrument and cauterization forceps of FIG. 11, showing the forceps in a retracted position.

FIGS. 11 and 12 illustrate another embodiment of an ultrasonic probe assembly including the instrument 20 of FIGS. 1-6 and a different RF cauterization forceps 106. Forceps 106 includes a pair of spring loaded prongs 108 and 109 each having a first bend 110 and a second bend 112 in the plane P3 of a forceps axis 114 and a probe axis 116, a third bend or curve 118 out of that plane and a fourth bend or curve 119 placing operative tips 120 and 122 of prongs 108 and 109 back towards the plane P3 of axes 114 and 116. Bend or curve 118 is approximately at the same longitudinal location as the second bend 112, while the fourth bend 119 or curve is located distally of the second and third bends 112 and 118. The first and second bends 110 and 112 conform the forceps 106 to probe casing 26, particularly housing 28 and sheath 30, while the other two bends 118 and 119 facilitate visualization during a cauterization operation by displacing a distal end portion of the forceps 106 away from the operating plane P3, i.e. the plane of axis 114 and 116. In an extended position of forceps 106 (FIG. 11), operative tips 120 and 122 are located more distally than operative tip 24 of probe probe 22.

Figure 13:
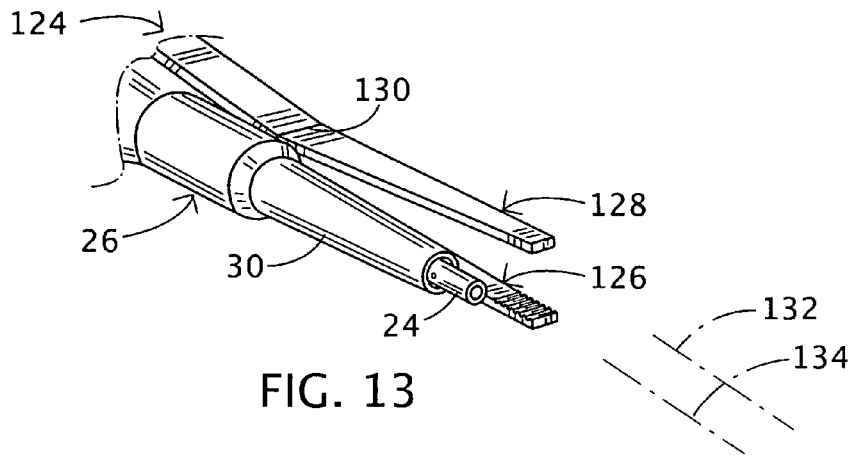
FIG. 13 is a schematic perspective view of a distal end portion of the ultrasonic instrument of FIGS. 1-7 with yet another modified detachable cauterization forceps, in accordance with the present invention, showing the forceps in an extended position.
Figure 14:
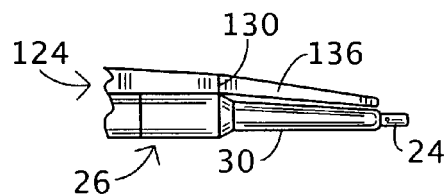
FIG. 14 is a partial top plan view of the ultrasonic instrument and cauterization forceps of FIG. 13, showing the forceps in a retracted position.

FIGS. 13 and 14 illustrate yet another embodiment of an ultrasonic probe assembly including the instrument 20 of FIGS. 1-6 and a different RF cauterization forceps 124. Forceps 124 includes a pair of spring loaded prongs 126 and 128 each having a first bend (not illustrated) and a second bend 130 in a plane including a forceps axis 132 and spaced laterally from a probe axis 134. A third bend or curve 136 displaces the distal end portions of prongs 126 and 128 out of that plane and towards sheath 30 (FIG. 14). All of the bends in this embodiment conform the forceps 124 to probe casing 26, particularly housing 28 (not shown in FIGS. 13, 14) and sheath 30.

Figure 15:
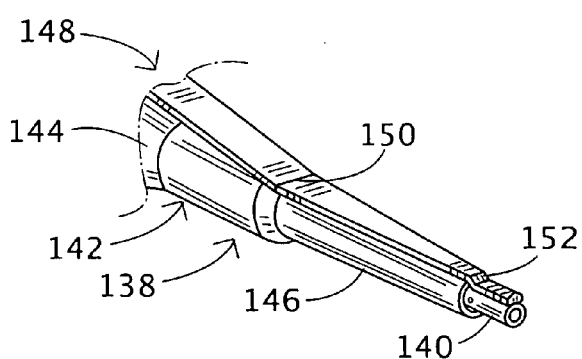
FIG. 15 is a schematic perspective view of a distal end portion of a modified ultrasonic instrument with a modified detachable cauterization forceps, in accordance with the present invention, showing the forceps in an extended position
Figure 16:
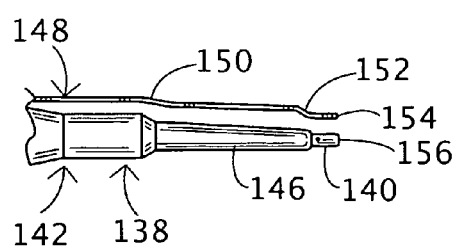
FIG. 16 is a partial side elevational view of the ultrasonic instrument and cauterization forceps of FIG. 15, showing the forceps in the extended position.

FIGS. 15 and 16 depict an embodiment of an ultrasonic probe assembly including an ultrasonic probe 138 with an ultrasonic horn 140 and a casing 142 having a proximal housing portion 144 and a distal sheath portion 146. A forceps member 148 includes a single prong (not separately enumerated) that is spring biased away from probe horn 140 and sheath 146 in an extended use position shown in the drawing. In this embodiment, probe 138, and particularly horn 140 thereof, acts as a second electrode. Forceps member or prong 148 is provided with stepped segments or bends 150, 152 conforming the prong to the tapered shape of the probe and ensuring that a distal operative tip 154 of the prong 148 is located adjacent to an operative tip 156 of horn 140.

In use, the forceps described hereinabove are attached to a casing 26, 142 of a respective instrument 20, 138 prior to a surgical procedure. The distal ends of the instrument 20, 138 and the forceps are inserted substantially simultaneously into a patient. Thereafter instrument 20, 138 is energized with a standing ultrasonic compression wave to ablate tissues of a patient. The forceps 36, etc., are manipulated to clamp tissues of the patient after the inserting of the distal ends of instrument 20 and forceps 36, etc., into the patient. Thereafter a radio-frequency electrical waveform is delivered to the forceps to cauterize the clamped tissues. After the surgical operations on the internal tissues has been completed, instrument 20, 138 together with the attached forceps is removed from the patient and the forceps are detached from the casing 26, 142. The clamping of the tissues is effectuated in part by pressing the outer prong against the inner prong or against the probe itself. Tab or nub 54 is pushed forwardly or distally to locate the forceps in the extended position or the retracted position, respectively.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A surgical device comprising:
a forceps member having at least one prong, said prong being formed as an electrode;
at least one electrical connector on said forceps member for operatively connecting said prong to an electrical power source; and
a mechanical connector attached to said forceps member for removably fastening said forceps member to a housing of an ultrasonic probe.

2. The surgical device defined in claim 1 wherein said probe has said housing at a proximal end and a sheath at a distal end, said sheath being connected to said housing and surrounding said probe at a distal end thereof, said forceps member being bent so that said prong conforms at a proximal end to said housing and at a distal end to said sheath.

3. The surgical device defined in claim 2 wherein said forceps member includes a proximal end portion having an axis, said prong having a distal end portion bent away from said axis to lie along one side thereof.

4. The surgical device defined in claim 3 wherein said probe has an axis, the axis of said probe and the axis of said proximal end portion of said forceps member defining a plane, said prong including a first bend in said plane so that said distal end portion of said prong extends away from the axis of said proximal end portion and towards the axis of said probe, said prong including a second bend so that said prong extends out of said plane.

5. The surgical device defined in claim 4 wherein said prong includes a third bend generally towards a distal tip of said probe.

6. The surgical device defined in claim 5 wherein said third bend is located distally of said second bend, said second bend being located distally of said first bend.

7. The surgical device defined in claim 6 wherein said prong has a distal tip distally advanced with respect to an operating tip of said probe in a distal position of said forceps member relative to said housing.

8. The surgical device defined in claim 4 wherein said prong has a distal tip located substantially laterally of an operating tip of said probe.

9. The surgical device defined in claim 4 wherein said second bend is located distally of said first bend.

10. The surgical device defined in claim 1 wherein said mechanical connector takes the form of a spring clip.

11. The surgical device defined in claim 10 wherein said spring clip has a slotted circular configuration.

12. The surgical device defined in claim 1 wherein said mechanical connector is adapted to movably fasten said forceps member to the housing of said probe.

13. The surgical device defined in claim 12 wherein said mechanical connector is adapted to slidably fasten said forceps member to the housing of said probe so that said forceps member is alternatively movable in a distal direction and a proximal direction parallel to an axis of said probe.

14. The surgical device defined in claim 13, further comprising a tab or nub on said forceps member at least in part for facilitating a sliding of said forceps member parallel to said axis.

15. The surgical device defined in claim 1 wherein said prong is protected with an electrically insulating material, said prong having a distal tip free of said insulating material.

16. A surgical device comprising:
an ultrasonic probe;
a casing disposed about said probe;
a forceps member having at least one prong, said prong being formed as an electrode;
at least one electrical connector on said forceps member for operatively connecting said prong to an electrical power source; and
a mechanical connector attached to said forceps member removably fastening said forceps member to said casing.

17. The surgical device defined in claim 16 wherein said casing includes a housing at a proximal end and a sheath surrounding said probe at a distal end of said casing, said forceps member being bent so that said prong conforms at a proximal end to said housing and at a distal end to said sheath.

18. The surgical device defined in claim 17 wherein said forceps member includes a proximal end portion having an axis, said prong being bent away from said axis to lie along one side thereof.

19. The surgical device defined in claim 18 wherein said probe has an axis, the axis of said probe and the axis of said proximal end portion defining a plane, said prong including a first bend in said plane such that a distal end portion of said prong extends away from the axis of said proximal end portion and towards the axis of said probe, said prong including a second bend so that said prong extends out of said plane.

20. The surgical device defined in claim 19 wherein said prong includes a third bend generally towards a distal tip of said probe.

21. The surgical device defined in claim 20 wherein said third bend is located distally of said second bend, said second bend being located distally of said first bend.

22. The surgical device defined in claim 21 wherein said forceps member is movably mounted to said housing by said mechanical connector, said prong having a distal tip distally advanced with respect to an operating tip of said probe in a distal or advanced position of said forceps member relative to said housing.

23. The surgical device defined in claim 19 wherein said prong has a distal tip located substantially laterally of an operating tip of said probe.

24. The surgical device defined in claim 19 wherein said second bend is located distally of said first bend.

25. The surgical device defined in claim 18 wherein said proximal end portion is disposed adjacent to said housing and a distal end portion of said prong is disposed adjacent to said sheath.

26. The surgical device defined in claim 17 wherein said mechanical connector is adapted to movably fasten said forceps member to the housing of said casing.

27. The surgical device defined in claim 26 wherein said mechanical connector is adapted to slidably fasten said forceps member to the housing of said casing so that said forceps member is alternately movable in a distal direction and a proximal direction parallel to an axis of said probe.

28. The surgical device defined in claim 27, further comprising a tab or nub on said forceps member for facilitating a sliding of said forceps member parallel to said axis.

29. The surgical device defined in claim 16 wherein said mechanical connector takes the form of a spring clip.

30. The surgical device defined in claim 29 wherein said spring clip has a slotted circular configuration.

31. The surgical device defined in claim 16 wherein said prong is protected with an electrically insulating material, said prong having a distal tip free of said insulating material.

32. The surgical device defined in claim 16 wherein said prong is one of two prongs of said forceps member, said prongs being spring biased into an open configuration, said casing and said forceps member having cooperating locking means for holding said prongs in a closed non-use configuration.

33. The surgical device defined in claim 32 wherein said forceps member is slidably mounted to said casing for shifting alternately in a distal direction and a proximal direction, said cooperating locking means including a tab on at least one of said casing and said forceps member and a shoulder on the other of said casing and said forceps member for holding said prongs in said closed non-use configuration when said forceps member is slid in a proximal direction relative to said casing.

34. A medical method comprising:
providing an ultrasonic probe having a casing;
providing a forceps member having at least one prong formed as an electrode;
attaching said forceps member to said casing;
inserting distal ends of said probe and said forceps member substantially simultaneously into a patient;
thereafter energizing said probe with a standing ultrasonic compression wave to ablate tissues of a patient;
after the inserting of the distal ends of said probe and said forceps member into the patient, manipulating said forceps member to clamp tissues of the patient;
thereafter delivering a radio-frequency electrical waveform to said forceps member to cauterize the clamped tissues;
removing the probe and the forceps member from the patient; and
thereafter detaching the forceps member from the casing.

35. The method defined in claim 34, further comprising moving said forceps member relative to said probe after the inserting of said probe and said forceps member into the patient and prior to the delivering of the radio-frequency electrical waveform to said forceps member.

36. The method defined in claim 35 wherein the moving of said forceps member includes sliding said forceps member in a distal direction along said casing.

37. The method defined in claim 34 wherein the manipulating of said forceps member includes pressing said prong against said probe, said probe functioning in part as a forceps prong.

* * * * *